(12) United States Patent
Filippini et al.

(10) Patent No.: US 9,204,656 B2
(45) Date of Patent: Dec. 8, 2015

(54) FUNGICIDAL COMPOSITIONS BASED ON COPPER SALTS

(75) Inventors: Lucio Filippini, Galliate (IT); Marilena Gusmeroli, Monza (IT); Silvia Mormile, Novara (IT); Matteo Santino Vazzola, Cogliate (IT)

(73) Assignee: ISAGRO S.P.A., Milan (IT)

( * ) Notice: Subject to any disclaimer, the term of this patent is extended or adjusted under 35 U.S.C. 154(b) by 1190 days.

(21) Appl. No.: 13/138,055

(22) PCT Filed: Dec. 29, 2009

(86) PCT No.: PCT/EP2009/009351
§ 371 (c)(1),
(2), (4) Date: Sep. 8, 2011

(87) PCT Pub. No.: WO2010/076038
PCT Pub. Date: Jul. 8, 2010

(65) Prior Publication Data
US 2011/0318427 A1 Dec. 29, 2011

(30) Foreign Application Priority Data
Jan. 2, 2009 (IT) .............................. MI2009A0001

(51) Int. Cl.
*A01N 59/20* (2006.01)
*A01N 25/14* (2006.01)
*A01N 37/40* (2006.01)
(52) U.S. Cl.
CPC ............. *A01N 59/20* (2013.01); *A01N 37/40* (2013.01); *A01N 25/14* (2013.01)

(58) Field of Classification Search
None
See application file for complete search history.

(56) References Cited

FOREIGN PATENT DOCUMENTS

WO    WO 03/043971 A1    5/2003
WO    WO 03/065810 A1    8/2003

OTHER PUBLICATIONS
PCT Search Report dated March 29, 2010.

*Primary Examiner* — Abigail Fisher
*Assistant Examiner* — Frank Choi
(74) *Attorney, Agent, or Firm* — Hedman & Costigan, P.C.; James V. Costigan; Kathleen A. Costigan

(57) ABSTRACT
Fungicidal compositions are described, comprising:
A) a copper salicylate having the following molecular formula (I):
$$C_7H_4O_3Cu.(H_2O)_n \qquad (I)$$
wherein n represents 0, 1, 2 or 3;
B) copper hydroxide $Cu(OH)_2$ (II);
C) a copper salt having the following formula (III):
$$3Cu(OH)_2.X(Y)_m \qquad (III)$$
wherein:
X represents cupric ion $Cu^{2+}$ or calcium ion $Ca^{2+}$;
Y means chloride ion $Cl^-$ or sulphate ion $SO_4^{2-}$;
m is an integer equal to 1 or 2;
optionally in the presence of dispersants, diluents, surfactants and/or co-formulants agronomically acceptable, and the relative agronomical formulations.
The use of these fungicidal compositions and agronomical formulations for the control of phytopathogenic fungi in agricultural crops, is also described.

16 Claims, No Drawings

FUNGICIDAL COMPOSITIONS BASED ON COPPER SALTS

The present invention relates to compositions based on copper salts and their use for the control of phytopathogenic fungi.

In particular, it relates to compositions based on copper salts capable of effectively controlling phytopathogenic fungi causing damage to crops of economic interest.

Copper hydroxide, copper oxychloride, cuprocalcic oxychloride, tribasic copper sulphate, Bordeaux mixture, are well-known active ingredients for being used individually, or in a mixture with other fungicides, in foliar application for the control of phytopathogenic fungi. These copper active ingredients are described, for example in "THE PESTICIDE MANUAL, 11th EDITION, BRITISH CROP PROTECTION COUNCIL, Pages 136, 268-270".

In spite of the acknowledged effectiveness of copper products in the control of numerous fungal diseases which affect important agricultural crops, due to growing concern for the undesired toxicological effects that their prolonged use can cause, the necessity of reducing the rates of metallic copper within well-defined limits has become particularly important in recent years.

European patent EP 1471787 describes fungicidal compositions with which it is possible to reduce the doses of use of copper by mixing copper hydroxide with at least one other inorganic copper salt, such as copper oxychloride, tribasic copper sulphate, Bordeaux mixture, cuprocalcic oxychloride. However, the reduction of metallic copper content which can be obtained with these compositions is still not satisfactory. The fungicidal range of action of these compositions is also limited to some fungi belonging to the group of Oomycetes (*Plasmopara viticola* in particular).

U.S. Pat. No. 4,075,326 describes fungicidal compositions in which inorganic copper salts are combined with copper salts of unsaturated dibasic organic acids. In spite of the claimed enhancing effects, the use of these compositions does not at all seem to lead to an actual reduction in the copper doses. Example 4 of this document, for example, describes the improved fungicidal activity against *Colletotrichum lagenarium* of a composition q consisting of 40% by weight of copper terephthalate (Cu content=27.8%), 20% by weight of a wettable powder of copper oxychloride (Cu content=41%), 40% by weight of a wettable powder of copper hydroxide (Cu content=54%). This composition q therefore has a total copper content equal to 27.8×0.4+41×0.2+54×0.4=40.92% by weight. The fungicidal activity of the composition q is compared with the fungicidal activity of copper terephthalate alone (composition I-1), whose copper content (27.8% by weight), is in fact lower than that of the mixture of the composition q. Furthermore, the increase in the activity observed for this ternary mixture with respect to the copper-organic product used alone, is in fact modest (10-20%), bearing in mind that the copper content of the composition q has an increase of 46% by weight.

The "in vitro" antimicrobial activity of copper salts of salicylic acid with respect to phytopathogenic fungi is also known, as described for example in "Pesticides", 1980, 14(10), pages 29-30 and in "Indian Journal of Microbiology", 1981, pages 331-334.

However, due to the reduced persistence, the occasional appearance of phytotoxicity phenomena and the reduced range of action, the practical use of these compounds as fungicides is not completely satisfactory, even when associated with compounds capable of increasing their action as systemic acquired resistance inducers (SAR) with respect to fungal diseases in plants, as described in international patent application WO 2005/094580.

The Applicant has now found ternary compositions comprising, in suitable ratios, a copper salicylate (in which the salicylic acid and copper are present in a molar ratio of about 1:1), copper hydroxide, another copper salt selected from copper oxychloride, tribasic copper sulphate, Bordeaux mixture, cuprocalcic oxychloride, which overcome the drawbacks described above for the compositions according to the state of the art. In particular, these ternary compositions show a surprisingly high fungicidal activity, which is exerted at a much lower dosage of copper than that of copper salicylate as such, and also with respect to that of the mixtures of inorganic copper salts described in European patent EP 1,471,787. These compositions also have a wider range of action and a more persistent efficacy, in addition to showing a reduced or null phytotoxicity which allows them to be safely used on important crops.

An object of the present invention therefore relates to fungicide compositions comprising:
A) a copper salicylate having the following molecular formula (I):

$$C_7H_4O_3Cu \cdot (H_2O)_n \quad (I)$$

wherein n represents 0, 1, 2 or 3;
B) copper hydroxide $Cu(OH)_2$ (II);
C) a copper salt having the following formula (III):

$$3Cu(OH)_2 \cdot X(Y)_m \quad (III)$$

wherein:
X represents cupric ion $Cu^{2+}$ or calcium ion $Ca^{2+}$;
Y means chloride ion $Cl^-$ or sulphate ion $SO_4^{2-}$;
m is an integer equal to 1 or 2;
optionally in the presence of dispersants, diluents, surfactants and/or co-formulants agronomically acceptable.

A further object of the present invention therefore relates to agronomical formulations comprising the above compositions and possible dispersants, diluents, surfactants and/or co-formulants agronomically acceptable.

In particular, the compounds having formula (III) can be selected from copper oxychloride [$3Cu(OH)_2 \cdot CuCl_2$], cuprocalcic oxychloride [$3Cu(OH)_2 \cdot CaCl_2$], tribasic copper sulphate [$3Cu(OH)_2 \cdot CuSO_4$], Bordeaux mixture [$3Cu(OH)_2 \cdot CaSO_4$].

Preferred compositions according to the present invention are those in which the compounds having formula (I), (II) and (III) have an equivalent copper ratios respectively varying from 0.2:1:0.3 to 2:1:3, preferably from 0.4:1:0.8 to 1.2:1:1.2.

Even more preferred compositions are those in which in the compound having formula (I) n represents 1 and the compounds having formula (I), (II) and (III) are present in equivalent copper ratios respectively varying from 0.2:1:0.3 to 2:1:3, preferably from 0.4:1:0.8 to 1.2:1:1.2.

Further preferred compositions are those in which in the compound having formula (I) n represents 1, the compound having formula (III) is copper oxychloride [$3Cu(OH)_2 \cdot CuCl_2$] or tribasic copper sulphate [$3Cu(OH)_2 \cdot CuSO_4$] and the compounds having formula (I), (II) and (III) are present in equivalent copper ratios respectively varying from 0.2:1:0.3 to 2:1:3, preferably from 0.4:1:0.8 to 1.2:1:1.2.

Specific preferred compositions are:
C1: copper salicylate $C_7H_4O_3Cu \cdot H_2O$+copper hydroxide+copper oxychloride in equivalent copper ratio 1:1:1;
C2: copper salicylate $C_7H_4O_3Cu \cdot H_2O$+copper hydroxide+copper oxychloride in equivalent copper ratio 0.4:1:1;
C3: copper salicylate $C_7H_4O_3Cu \cdot H_2O$+copper hydroxide+copper oxychloride in equivalent copper ratio 0.6:1:1;

C4: copper salicylate $C_7H_4O_3Cu.H_2O$+copper hydroxide+ copper oxychloride in equivalent copper ratio 0.8:1:1;
C5: copper salicylate $C_7H_4O_3Cu.H_2O$+copper hydroxide+ copper oxychloride in equivalent copper ratio 0.4:1:1.2;
C6: copper salicylate $C_7H_4O_3Cu.H_2O$+copper hydroxide+ copper oxychloride in equivalent copper ratio 0.8:1:1.2;
C7: copper salicylate $C_7H_4O_3Cu.H_2O$+copper hydroxide+ copper oxychloride in equivalent copper ratio 1.2:1:0.8;
C8: copper salicylate $C_7H_4O_3Cu.H_2O$+copper hydroxide+ copper oxychloride in equivalent copper ratio 2:1:0.3;
C9: copper salicylate $C_7H_4O_3Cu.H_2O$+copper hydroxide+ copper oxychloride in equivalent copper ratio 0.2:1:3;
C10: copper salicylate $C_7H_4O_3Cu$+copper hydroxide+copper oxychloride in equivalent copper ratio 0.4:1:1;
C11: copper salicylate $C_7H_4O_3Cu$.+copper hydroxide+copper oxychloride in equivalent copper ratio 1:1:1;
C12: copper salicylate $C_7H_4O_3Cu.H_2O$+copper hydroxide+ tribasic copper sulphate in equivalent copper ratio 0.4:1:1;
C13: copper salicylate $C_7H_4O_3Cu.H_2O$+copper hydroxide+ tribasic copper sulphate in equivalent copper ratio 1:1:1;
C14: copper salicylate $C_7H_4O_3Cu.H_2O$+copper hydroxide+ tribasic copper sulphate in equivalent copper ratio 0.7:1:1;
C15: copper salicylate $C_7H_4O_3Cu.H_2O$+copper hydroxide+ Bordeaux mixture in equivalent copper ratio 1:1:1;
C16: copper salicylate $C_7H_4O_3Cu.H_2O$+copper hydroxide+ cuprocalcic oxychloride in equivalent copper ratio 1:1:1;
C17: copper salicylate $C_7H_4O_3Cu.2H_2O$+copper hydroxide+ copper oxychloride in equivalent copper ratio 1:1:1;
C18: copper salicylate $C_7H_4O_3Cu.3H_2O$+copper hydroxide+ copper oxychloride in equivalent copper ratio 1:1:1.

The preparation of the compositions object of the present invention can be effected according to different methods, also depending on the fact that these compositions only comprise copper salts, or are in the form of suitable agronomical formulations.

In the former case, the compositions according to the present invention are obtained by mechanically mixing suitable quantities of copper salicylate having formula (I), copper hydroxide (II) and copper salt having formula (III), already prepared individually.

The copper hydroxide (II) and copper salt having formula (III) are commercially available as technical products.

The copper salicylate having formula (I) can be prepared in various ways, for example by reacting salicylic acid in an aqueous medium with a base and subsequently adding a soluble copper salt, such as, for example, copper sulphate, or by reacting salicylic acid directly with a basic copper salt such as copper carbonate or copper hydroxide.

Alternatively, if the copper salt used for the preparation of the compound having formula (I) is copper hydroxide, the compositions of the present invention can be prepared by adding salicylic acid to copper hydroxide (II) in a suitable molar ratio and subsequently adding the copper salt having formula (III).

Further, the compositions of the present invention can also be prepared by adding salicylic acid as such to the mixture of copper hydroxide (II) and the copper salt having formula (III) in a suitable molar ratio.

If the compositions are in the form of suitable agronomical formulations, they can be wettable powders, granules, granules dispersible in water, concentrated suspensions, etc.

They can be prepared either by formulating the copper salts already mixed in suitable proportions together, or by mixing the salts formulated separately, in any order.

Further, during the preparation of the formulations, salycilic acid as such can be added to the mixture of copper hydroxide (II) and the copper salt having formula (III), in a suitable molar ratio.

Solid diluents which can be used in the formulations are, for example: silica, kaolin, bentonite, talc, infusorial earth, dolomite, calcium carbonate, magnesia, gypsum, clays, synthetic silicates, attapulgite, seppiolite.

Liquid diluents which can be used are, for example: water, aromatic or paraffinic organic solvents, alcohols, esters, ketones, amides.

Surfactants which can be used are, for example: salts of sodium, potassium, triethanolamine of alkyl naphthalenesulphonates, polynaphthalenesulphonates, phenyl sulphonates, polycarboxylates, sulfosuccinates, alkyl sulfosuccinates, alkyl sulphates, lignin sulphonates, alkylaryl sulphonates; and again, polyethoxylated fatty alcohols, polyethoxylated alkylphenols, polyethoxylated esters of sorbitol, polypropoxy polyethoxylates (block polymers) can also be used.

The compositions can also contain special additives for particular purposes, for example antifreeze agents such as propylene glycol, or adhesives such as Arabic gum, polyvinyl alcohol, polyvinyl pyrrolidone, etc.

In the phytosanitary formulations according to the present invention, the percentage content of equivalent metallic copper coming from the ternary mixture of copper salts having formula (I), (II) and (III) can vary from 3% to 50%, preferably from 10% to 35%.

As already specified, the compositions, object of the present invention, exert a surprisingly high fungicidal activity, compared with the activities of the components used individually.

A further object of the present invention therefore relates to the use of fungicidal compositions comprising:
A) a copper salicylate having the following molecular formula (I):

$$C_7H_4O_3Cu.(H_2O)_n \quad (I)$$

wherein n represents 0, 1, 2 or 3;
B) copper hydroxide $Cu(OH)_2$ (II);
C) a copper salt having the following formula (III):

$$3Cu(OH)_2.X(Y)_m \quad (III)$$

wherein:
X represents cupric ion $Cu^{2+}$ or calcium ion $Ca^{2+}$;
Y means chloride ion $Cl^-$ or sulphate ion $SO_4^{2-}$;
m is an integer equal to 1 or 2;
optionally in the presence of dispersants, diluents, surfactants and/or co-formulants agronomically acceptable, for the control of phytopathogenic fungi in agricultural crops.

An object of the present invention also relates to a method for the control of phytopathogenic fungi in agricultural crops by the application of a fungicidal composition as previously defined.

Examples of phytopathogenic fungi which can be effectively controlled with the fungicidal compositions or with the agronomical formulations according to the present invention are: *Plasmopara viticola* on vines, *Phytophthora* spp. on vegetables, *Pseudoperonospora cubensis* on cucurbits, *Peronospora tabacina* on tobacco, *Bremia lactucae* on salads and spinach, *Venturia* spp. on fruit trees, *Uromyces appendiculatus* on beans, *Alternaria* spp. on vegetables and fruit trees, *Sphaeroteca fuliginea* on cucurbits, *Erysiphe* spp. on vegetables and cereals.

The compositions of the present invention can also be effectively used for the control of bacteria and phytopathogenic viruses.

The fungicidal compositions or phytosanitary formulations according to the present invention can be used in agronomic practice for applications on plants or on a part of them, in particular on all parts of the plant, leaves, stems, branches and roots.

The fungicidal compositions or phytosanitary formulations according to the present invention can be conveniently used in agronomic practice alone or, in order to broaden their range of action, in association with other fungicidal active ingredients.

For illustrative purposes and without any limitative intent, some of the active ingredients which can be conveniently used in a mixture with the compositions or formulations object of the present invention, are listed hereunder:
amisulbrom, benalaxyl, benalaxyl-M, benthiavalicarbisopropyl, captane, cyazofamid, cymoxanil, dinocap, chlorotalonil, dimethomorph, ethaboxam, etridiazole, famoxadone, fenamidone, fluazinam, flumorph, fluopicolide, folpet, fosetyl-aluminium, furalaxyl, hymenaxol, iprovalicarb, mandipropamid, metalaxyl, metalaxyl-M, ofurace, oxadixyl, pencicuron, procimidone, propamocarb, prothiocarb, sulphur, tiram, tolclofos methyl, valifenalate (IR5885), zoxamide.

The following examples are provided for illustrative and non-limiting purposes of the present invention.

EXAMPLE 1

Preparation of Copper Salicylate $C_7H_4O_3Cu.H_2O$ (I-1)

70.6 g (0.724 moles) of $Cu(OH)_2$ were added in portions to a suspension of 100 g (0.724 moles) of salicylic acid in 1 liter of water, and the mixture was left under stirring at room temperature for 2 hours. The stirring system must be adequate in that, as the reaction proceeds and the pH increases to the final value of about 6, the viscosity increases. The colour changes from green to ochre of the final product. The reaction mixture was then filtered on a buchner and dried in air, obtaining 148 g of the desired product (MW=217.5).

The reaction mixture can also be used as slurry ready for the subsequent formulation (Example 7). Elemental analysis %: C=38.85 (theoretical 38.71); H=2.65 (theoretical 2.70); Cu=29.10 (theoretical 29.2).

EXAMPLE 2

Preparation of Copper Salicylate $C_7H_4O_3Cu.H_2O$ (I-1)

A solution of NaOH, 58 g (1.45 moles) in 300 ml, was added to a suspension of 100 g (0.724 moles) of salicylic acid in 400 ml of water, until a complete dissolution was obtained. An aqueous solution of $CuSO_4$, 180.8 g (0.724 moles) in 300 ml, was then added and the mixture was left under stirring at room temperature for 8 hours. The stirring system must be adequate in that, as the reaction proceeds and the pH increases to the final value of about 6, a fine green solid precipitates whose colour subsequently changes to ochre of the final product, and the viscosity increases.

The reaction mixture was then filtered on a buchner, washed with water (500 ml) and dried in air, obtaining 150 g of the desired product.

Elemental analysis %: C=38.80 (theoretical 38.71); H=2.60 (theoretical 2.70); Cu=29.10 (theoretical 29.2).

EXAMPLE 3

Preparation of the Mixture Copper Salicylate $C_7H_4O_3Cu.H_2O$ (I-1)+Copper Hydroxide (II) in an Equivalent Copper Ratio of 1:1

141.3 g (1.447 moles) of $Cu(OH)_2$ were added in portions to a suspension of 100 g (0.724 moles) of salicylic acid in 1 liter of water, and the mixture was left under stirring at room temperature for 4 hours. The reaction mixture was then filtered on a buchner and dried in air, obtaining 215 g of the desired product (elemental analysis).

The reaction mixture can also be used as slurry ready for the subsequent formulation.

EXAMPLE 4

Preparation of the Composition C1

Copper Salicylate $C_7H_4O_3Cu.H_2O$ (I-1)+Copper Hydroxide (II)+Copper Oxychloride (III-1) in an Equivalent Copper Ratio of 1:1:1

70.6 g (0.724 moles) of $Cu(OH)_2$ were added in portions to a suspension of 100 g (0.724 moles) of salicylic acid in 1.5 liters of water, and the mixture was left under stirring at room temperature for 2 hours. The stirring system must be adequate in that, as the reaction proceeds and the pH increases to the final value of about 6, the viscosity increases. The colour changes from green to ochre of the final product. At this point, a further 70.6 g (0.724 moles) of $Cu(OH)_2$ and 77.3 g (0.181 moles) of copper oxychloride $3Cu(OH)_2.CuCl_2$ (corresponding to 0.724 equivalents of copper), were added and the mixture was left under stirring for 30 minutes. The reaction mixture was then filtered on a buchner and dried in air, obtaining 290 g of the desired mixture (elemental analysis).

The reaction mixture can also be used as slurry ready for the subsequent formulation.

EXAMPLE 5

Preparation of the Composition C2

Copper Salicylate $C_7H_4O_3Cu.H_2O$ (I-1)+Copper Hydroxide (II)+Copper Oxychloride (III-1) in an Equivalent Copper Ratio of 0, 4:1:1

40 g (0.289 moles) of salicylic acid were added to a suspension of 98.8 g (1.014 moles) of $Cu(OH)_2$ and 77.3 g (0.181 moles) of copper oxychloride $3Cu(OH)_2.CuCl_2$ (corresponding to 0.724 equivalents of copper),in 1.5 liters of water; the mixture was left under stirring at room temperature for 4 hours. The reaction mixture was then filtered on a buchner and dried in air, obtaining 192 g of the desired mixture (elemental analysis).

The reaction mixture can also be used as slurry ready for the subsequent formulation.

EXAMPLE 6

Preparation of Copper Salicylate $C_7H_4O_3Cu.H_2O$ as a Wet-Table Powder (WP): I-1/WP A formulation of the wettable powder type was prepared by suitably mixing and grinding the following ingredients:

| INGREDIENTS | QUANTITY % (wt/wt) |
|---|---|
| Technical copper salicylate at 99% (Cu content = 29%) | 50.5 (equal to 14.6% of Cu) |
| Sodium alkyl naphthalenesulphonate | 1.5 |
| Sodium polycarboxylate | 1.0 |
| Sodium ligninsulphonate | 3.0 |
| Silica | 1.0 |
| Calcium carbonate | Complement to 100 |

EXAMPLE 7

Preparation of Copper Salicylate $C_7H_4O_3Cu.H_2O$ as Dispersible Granules (WG): I-1/WG A formulation of the dispersible granule type, at 20% of copper (WG), was prepared by adding the following ingredients to the slurry obtained as described in Example 1:

| INGREDIENTS | QUANTITY (g) |
|---|---|
| Sodium alkyl naphthalenesulphonate | 2.3 |
| Sodium polynaphthalenesulphonate | 9.1 |
| Calcium ligninsulphonate | 11.4 |
| Kaolin | 48 |

The slurry thus prepared was granulated by evaporation of the water present (fluid bed granulation), obtaining the final dispersible granule (WG) having the following composition:

| INGREDIENTS | QUANTITY % (wt/wt) |
|---|---|
| Technical copper salicylate at 99% (Cu content = 29%) | 69.0 (equal to 20% of Cu) |
| Sodium alkyl naphthalenesulphonate | 1.0 |
| Sodium polycarboxylate | 4.0 |
| Calcium ligninsulphonate | 5.0 |
| Kaolin | Complement to 100 |

EXAMPLE 8

Preparation of the Mixtures Copper Hydroxide+Copper Oxychloride in an Equivalent Copper Ratio of 1:1, as a Wettable Powder (WP): CHCO-1/WP A formulation of the wettable powder type at 50% of copper (WP 50) was prepared by suitably mixing and grinding the following ingredients:

| INGREDIENTS | QUANTITY % (wt/wt) |
|---|---|
| Technical copper hydroxide at 93.7% (Cu content = 61%) | 41.0 (equal to 25% of Cu) |
| Technical copper oxychloride at 96.6% (Cu content = 57.5%) | 43.5 (equal to 25% of Cu) |
| Sodium alkyl naphthalenesulphonate | 1.5 |
| Sodium polycarboxylate | 1.0 |
| Sodium ligninsulphonate | 3.0 |
| Silica | 1.0 |
| Calcium carbonate | 9.0 |

EXAMPLE 9

Preparation of the Mixture Copper Hydroxide+Copper Oxychloride in an Equivalent Copper Ratio of 1:1, as Dispersible Granules (WG): CHCO-1/WG A formulation of the dispersible granule type at 50% of copper (WG) was prepared by suitably mixing, grinding and granulating the following ingredients:

| INGREDIENTS | QUANTITY % (wt/wt) |
|---|---|
| Technical copper hydroxide at 93.7% (Cu content = 61%) | 41.0 (equal to 25% of Cu) |
| Technical copper oxychloride at 96.6% (Cu content = 57.5%) | 43.5 (equal to 25% of Cu) |
| Sodium alkyl naphthalenesulphonate | 1.0 |
| Sodium laurylsulphate | 2.0 |
| Sodium ligninsulphonate | 8.0 |
| Kaolin | Complement to 100 |

EXAMPLE 10

Preparation of the Composition C2

Copper Salicylate $C_7H_4O_3Cu.H_2O$+Copper Hydroxide+Copper Oxychloride in an Equivalent Copper Ratio of 0.4:1:1, as a Wettable Powder (WP): C2/WP A formulation of the wettable powder type at 30% of copper (WP) was prepared by suitably mixing and grinding the following ingredients:

| INGREDIENTS | QUANTITY % (wt/wt) |
|---|---|
| Technical copper salicylate at 99% (Cu content = 29%) | 17.2 (equal to 5% of Cu) |
| Technical copper hydroxide at 93.7% (Cu content = 61%) | 20.5 (equal to 12.5% of Cu) |
| Technical copper oxychloride at 96.6% (Cu content = 57.5%) | 21.7 (equal to 12.5% of Cu) |
| Sodium alkyl naphthalenesulphonate | 1.5 |
| Sodium polycarboxylate | 1.0 |
| Sodium ligninsulphonate | 5.0 |
| Silica | 1.0 |
| Calcium carbonate | Complement to 100 |

Analogously, by suitably dosing the ratios of copper salicylate, copper hydroxide and copper oxychloride, a wettable powder formulation was prepared with copper at 30% of copper salicylate $C_7H_4O_3Cu.H_2O$ (I-1)+copper (II) hydroxide+copper (III-1) oxychloride in an equivalent copper ratio of 1:1:1; C1/WP.

EXAMPLE 11

Preparation of the Composition C1

Copper Salicylate $C_7H_4O_3Cu.H_2O$+Copper Hydroxide+Copper Oxychloride in an Equivalent Copper Ratio of 1:1:1, as Dispersible Granules (WG): C1/WG A further WG formulation was prepared as described in Example 8 starting from the following ingredients:

| INGREDIENTS | QUANTITY % (wt/wt) |
|---|---|
| Technical copper salicylate at 99% (Cu content = 29%) | 34.5 (equal to 10% of Cu) |
| Technical copper hydroxide at 93.7% (Cu content = 61%) | 16.4 (equal to 10% of Cu) |
| Technical copper oxychloride at 96.6% (Cu content = 57.5%) | 17.4 (equal to 10% of Cu) |
| Sodium alkyl naphthalenesulphonate | 1.0 |
| Sodium polynaphthalenesulphonate | 4.0 |
| Calcium ligninsulphonate | 6.0 |
| Calcium carbonate | Complement to 100 |

EXAMPLE 12

Greenhouse Preventive Activity (7 Days) Against *Plasmopara viticola* on vines Vine leaves (cultivar Barbera), grown in a vase in a conditioned environment at 24° C. and at 60% of R.H. (Relative Humidity), were treated by spraying both sides with the products being tested.

7 days after the treatment, the plants were inoculated with an aqueous suspension of conidia of *Plasmopara viticola* (200.000 conidia/cc) by spraying the lower side with a compressed air gun.

After remaining 24 hours in a humidity-saturated environment at 21° C., the plants were transferred for the incubation period (7 days) to a conditioned environment at 70% of R.H. and 21° C.

After this period the external symptoms of the pathogen appeared and it was therefore possible to proceed with an evaluation of the intensity of the infection, by means of a visual evaluation scale of the percentage of unaffected leaf area; the scale comprises the value 100 (healthy plant) and the value 0 (completely infected plant) as extremes.

The Table indicates the results obtained for the following products/compositions:

I-1/WP: wettable powder formulation at 50% (14.6% of copper) of the copper salicylate $C_7H_4O_3Cu.H_2O$ (I-1), described in Example 5;
CHCO-1/WP: wettable powder formulation with copper at 50%, of copper hydroxide (II)+copper (III-1) oxychloride in an equivalent copper ratio of 1:1, described in Example 8
C1/WP: wettable powder formulation with copper at 30%, of copper salicylate $C_7H_4O_3Cu.H_2O$ (I-1)+copper hydroxide (II)+copper oxychloride (III-1) in an equivalent copper ratio of 1:1:1, described in Example 10;
C2/WP: wettable powder formulation with copper at 30%, of copper salicylate $C_7H_4O_3Cu.H_2O$ (1-1)+copper hydroxide (II)+copper oxychloride (III-1) in an equivalent copper ratio of 0.4:1:1, described in Example 10;

The synergistic effect for the compositions was evaluated by comparing the activities obtained with those expected by both applying the Limpel formula, adapted to ternary mixtures, and also considering the additive effects of the components.

According to the Limpel formula ("Pesticide Science" (1987), vol. 19, pages 309-315):

$$E_{exp}=E_I+E_{II+III}-(E_I \times E_{II+III}/100)$$

wherein:
$E_{exp}$ is the fungicidal activity expected from a mixture obtained by mixing component (I) at a dose $D_I$ and components (II)+(III) at a dose $D_{II+III}$;
$E_I$ is the activity observed of component (I) when used alone at a dose $D_I$;
$E_{II+III}$ is the activity observed of the mixture (II)-(III) when used alone at a dose $D_{II+III}$.
Considering the additive effects:

$$E_{add}=E_I E_{II+III}$$

A synergistic effect is present when the activities observed $E_{obs}$ for the compositions are higher than those expected $E_{exp}$ and $E_{add}$.

From the results, it is evident the considerable increase in the fungicidal activity obtained for the compositions C1 and C2 with respect to the expected activities. The strong synergistic effect of compositions C1 and C2 is further confirmed by comparing the activities observed at 30 ppm copper rate for C1/WP, C2/WP, I-1/WP, CHCO-1/WP.

TABLE

Greenhouse preventive activity (7 days) against *Plasmopara viticola* on vines.

| Product | Dose of Cu (ppm) | $E_{obs}$ | $E_{exp}$ | $E_{add}$ |
|---|---|---|---|---|
| I-1/WP | 5 | 12 | | |
|  | 10 | 18 | | |
|  | 30 | 36 | | |
| CHCO-1/WP | 20 | 35 | | |
|  | 25 | 42 | | |
|  | 30 | 56 | | |
| C1/WP | 30 | 100 | 46.7 | 53 |
| C2/WP | 30 | 100 | 49 | 54 |

The invention claimed is:

1. Fungicidal compositions comprising:
   A) a copper salicylate having the following molecular formula (I): $C_7H_4O_3Cu.(H_2O)_n$ wherein n represents 0, 1, 2, 3;
   B) copper hydroxide $Cu(OH)_2$ (II);
   C) a copper salt having the following formula (III):

$$3Cu(OH)_2 \cdot X(Y)_m \quad \text{(III)}$$

wherein:
   X represents cupric ion $Cu^{2+}$;
   Y means chloride ion $Cl^-$;
   m is an integer equal to 2; optionally in the presence of dispersants, diluents, surfactants and/or agronomically acceptable co-formulants.

2. Fungicidal compositions according to claim 1, characterized in that the compounds of formulae (I), (II) and (III) exist in equivalent copper ratios ranging from 0.2:1:0.3 to 2:1:3.

3. Fungicidal compositions according to claim 1, characterized in that the compounds of formulae (I), (II) and (III) exist in equivalent copper ratios ranging from 0.4:1:0.8 to 1.2:1:1.2.

4. Fungicidal compositions according to claim 1, characterized in that the compound of formula (I) has n equal to 1 and the compounds of formulae (I) (II) and (III) exist in equivalent copper ratios ranging from 0:2:1:0.3 to 2:1:3.

5. Fungicidal compositions according to claim 1, characterized in that, the compound of formula (I) has n equal to 1 and the compounds of formulae (I), (II) and (III) exist in equivalent copper ratios ranging from 0.4:1:0.8 to 1.2:1:1.2.

6. Fungicidal compositions according to claim 1, characterized in that they are selected from the group consisting of:
   copper salicylate: $C_7H_4O_3Cu.H_2O$+copper hydroxide+copper oxychloride in equivalent copper ratio 1:1:1;
   copper salicylate $C_7H_4O_3Cu.H_2O$+copper hydroxide+copper oxychloride in equivalent copper ratio 0.4:1:1;

copper salicylate $C_7H_4O_3Cu.H_2O$+copper hydroxide+ copper oxychloride in equivalent copper ratio 0.6:1:1;
copper salicylate $C_7H_4O_3Cu.H_2O$+copper hydroxide+ copper oxychloride in equivalent copper ratio 0.8:1:1;
copper salicylate $C_7H_4O_3Cu.H_2O$+copper hydroxide+ copper oxychloride in equivalent copper ratio 0.4:1:1.2;
copper salicylate $C_7H_4O_3Cu.H_2O$+copper hydroxide+ copper oxychloride in equivalent copper ratio 0.8:1:1.2;
copper salicylate $C_7H_4O_3Cu.H_2O$+copper hydroxide+ copper oxychloride in equivalent copper ratio 1.2:1:0.8;
copper salicylate $C_7H_4O_3Cu.H_2O$+copper hydroxide+ copper oxychloride in equivalent copper ratio 2:1:0.3;
copper salicylate $C_7H_4O_3Cu.H_2O$+copper hydroxide+ copper oxychloride in equivalent copper ratio 0.2:1:3;
copper salicylate $C_7H_4O_3Cu$+copper hydroxide+copper oxychloride, in equivalent copper ratio 0.4:1:1;
copper salicylate $C_7H_4O_3Cu$+copper hydroxide+copper oxychloride in equivalent copper ratio 1:1:1;
copper salicylate $C_7H_4O_3Cu.2H_2O$+copper hydroxide+ copper oxychloride ire equivalent copper ratio 1:1:1; and
copper salicylate $C_7H_4O_3Cu.3H_2O$+copper hydroxide+ copper oxychloride equivalent copper ratio 1:1:1.

7. Phytosanitary formulations comprising the fungicidal compositions according to claim 1 and dispersants, diluents, surfactants or agronomically acceptable co-formulants.

8. Agronomical formulations according to claim 7, characterized in that they are wettable powders, granules, water-dispersible granules or concentrated suspensions.

9. Agronomical formulations according to claim 7, characterized in that they further contain antifreeze agents.

10. Agronomical formulations according to claim 7, characterized in that they further contain adhesives.

11. Agronomical formulations according to claim 7, characterized in that the equivalent percentage content of copper metal from the ternary mixture of cupric salts of formulae (I), (II) and (III) can range from 3% by weight to 50% by weight.

12. Agronomical formulations according to claim 7, characterized in that the equivalent percentage content of copper metal from the ternary mixture of cupric salts of formulae (I), (II) and (III) can range from 10% by weight to 35% by weight.

13. A method of controlling phytopathogenic fungi on agricultural crops comprising the application of fungicidal compositions to said agricultural crops where said fungicidal compositions comprise:
    A) a copper salicylate having the following molecular formula (I):

    $$C_7H_4O_3Cu.(H_2O)_n \quad (I)$$

wherein n represents 0, 1, 2 or 3;
    B) copper hydroxide $Cu(OH)_2$ (II);
    C) a copper salt having the following formula (III):

    $$3Cu(OH)_2.X(Y)_m, \quad (III)$$

wherein:
    X represents cupric ion $Cu^{2+}$;
    Y means chloride ion $Cl^-$;
    m is an integer equal to 2; optionally in the presence of dispersants, diluents, surfactants and/or agronomically acceptable co-formulants.

14. A method for the control of phytopathogenic fungi in agricultural crops comprising the application of a fungicidal composition as defined in claim 1 to said agricultural crops.

15. A method of controlling phytopathogenic fungi on agricultural crops comprising the application of fungicidal compositions according to claim 2 to said agricultural crops.

16. A method of controlling phytopathogenic fungi on agricultural crops comprising the application of agronomical formulations according to claim 7 for to said agricultural crops.

* * * * *